(12) United States Patent
Raykhman et al.

(10) Patent No.: US 9,816,848 B2
(45) Date of Patent: Nov. 14, 2017

(54) METHOD AND APPARATUS FOR NON-INVASIVELY MEASURING PHYSICAL PROPERTIES OF MATERIALS IN A CONDUIT

(71) Applicant: ULTIMO MEASUREMENT LLC, Scituate, RI (US)

(72) Inventors: Alexander M. Raykhman, East Greenwich, RI (US); Francis M. Lubrano, Scituate, RI (US)

(73) Assignee: ULTIMO MEASUREMENT LLC, Scituate, RI (US)

( * ) Notice: Subject to any disclaimer, the term of this patent is extended or adjusted under 35 U.S.C. 154(b) by 93 days.

(21) Appl. No.: 14/604,455

(22) Filed: Jan. 23, 2015

(65) Prior Publication Data

US 2015/0212045 A1    Jul. 30, 2015

Related U.S. Application Data

(60) Provisional application No. 61/930,611, filed on Jan. 23, 2014.

(51) Int. Cl.
*G01F 1/86*    (2006.01)
*G01N 29/44*    (2006.01)
(Continued)

(52) U.S. Cl.
CPC ............ *G01F 1/86* (2013.01); *E21B 41/0007* (2013.01); *G01F 1/002* (2013.01); *G01F 1/66* (2013.01);
(Continued)

(58) Field of Classification Search
CPC ........ G01F 1/86; G01F 1/002; E21B 41/0007; G01N 29/02; G01N 29/024
See application file for complete search history.

(56) References Cited

U.S. PATENT DOCUMENTS

| 4,117,716 A | 10/1978 | Simon |
| 4,182,177 A | 1/1980 | Prough |

(Continued)

FOREIGN PATENT DOCUMENTS

| CN | 1107231 A | 8/1995 |
| CN | 1930454 A | 3/2007 |

(Continued)

OTHER PUBLICATIONS

A Paradigm Here is Provided by the Famous Burgers Equation [ Dave Harris proposal at www.maths.manchester.ac.uk/~dh/MScProjects/NumAnalProj07.html, en.wikipedia.org/wiki/Burger%27_equation ].

(Continued)

*Primary Examiner* — Peter Macchiarolo
*Assistant Examiner* — Timothy Graves
(74) *Attorney, Agent, or Firm* — Lando & Anastasi, LLP

(57) ABSTRACT

Methods and apparatus for non-invasive determination of one or more physical properties of a material in a conduit are presented. In one example, the method comprises initiating a vibration on a wall of the conduit at a first location, capturing a response to the vibration at the first location, capturing a response to the vibration at a second location, and determining at least one physical property of the material based on at least one of the captured responses at the first location and the second location.

16 Claims, 10 Drawing Sheets

3. Striker - Receiver Module
4. Remote Receiver of Content Material Spherical Wave (Longitudinal Propagation)
5. Data Processing Module
6. Sensor Registry for Spherical Wave (Transverse Direction of Propagation)

(51) Int. Cl.
*G01F 1/00* (2006.01)
*G01F 1/66* (2006.01)
*G01F 1/74* (2006.01)
*G01N 29/024* (2006.01)
*G01N 9/24* (2006.01)
*G01N 11/16* (2006.01)
*E21B 41/00* (2006.01)
G01F 23/296 (2006.01)
G01N 11/00 (2006.01)

(52) U.S. Cl.
CPC .............. *G01F 1/74* (2013.01); *G01N 9/24* (2013.01); *G01N 11/16* (2013.01); *G01N 29/024* (2013.01); *G01N 29/4472* (2013.01); *G01F 23/296* (2013.01); *G01F 23/2962* (2013.01); *G01N 2011/006* (2013.01); *G01N 2291/02818* (2013.01); *G01N 2291/02836* (2013.01); *G01N 2291/0421* (2013.01); *G01N 2291/106* (2013.01)

(56) References Cited

U.S. PATENT DOCUMENTS

| | | | |
|---|---|---|---|
| 4,292,522 A | 9/1981 | Okumoto |
| 4,506,541 A | 3/1985 | Cunningham |
| 4,574,328 A | 3/1986 | Maier |
| 4,896,536 A | 1/1990 | Benz |
| 4,954,997 A | 9/1990 | Dieulesaint et al. |
| 5,015,995 A | 5/1991 | Holroyd |
| 5,110,208 A | 5/1992 | Sreepada et al. |
| 5,207,098 A | 5/1993 | Koch et al. |
| 5,261,274 A | 11/1993 | Nemirow |
| 5,359,541 A | 10/1994 | Pope et al. |
| 5,531,639 A | 7/1996 | Catalfamo |
| 5,610,611 A | 3/1997 | McEwan |
| 5,631,633 A | 5/1997 | Dreyer et al. |
| 5,686,661 A | 11/1997 | Singh et al. |
| 5,699,151 A | 12/1997 | Akasu |
| 5,755,136 A | 5/1998 | Getman et al. |
| 5,793,704 A | 8/1998 | Freger |
| 5,807,092 A | 9/1998 | Mifune et al. |
| 5,822,275 A | 10/1998 | Michalski |
| 5,862,431 A | 1/1999 | Christensen |
| 5,877,997 A | 3/1999 | Fell |
| 5,892,576 A | 4/1999 | Gaechter |
| 6,040,898 A | 3/2000 | Mrosik et al. |
| 6,053,041 A * | 4/2000 | Sinha ................. G01F 23/28 340/621 |
| 6,105,425 A | 8/2000 | Kawakatsu |
| 6,111,211 A | 8/2000 | Dziedzic et al. |
| 6,122,602 A | 9/2000 | Michalski et al. |
| 6,128,982 A | 10/2000 | Gwin, Sr. |
| 6,166,995 A | 12/2000 | Hoenes |
| 6,192,751 B1 | 2/2001 | Stein et al. |
| 6,194,215 B1 | 2/2001 | Rauh et al. |
| 6,216,059 B1 | 4/2001 | Ierymenko |
| 6,448,782 B1 | 9/2002 | Pakonen et al. |
| 6,452,467 B1 | 9/2002 | McEwan |
| 6,472,887 B1 | 10/2002 | Tullis et al. |
| 6,481,276 B1 | 11/2002 | Neuhaus et al. |
| 6,539,794 B1 | 4/2003 | Otto et al. |
| 6,631,639 B1 * | 10/2003 | Dam .................. G01F 23/2961 340/621 |
| 6,738,044 B2 | 5/2004 | Holzrichter et al. |
| 6,738,720 B2 | 5/2004 | Odom et al. |
| 6,945,094 B2 | 9/2005 | Eggen et al. |
| 7,059,171 B2 | 6/2006 | Gysling |
| 7,059,176 B2 | 6/2006 | Sparks |
| 7,103,500 B2 | 9/2006 | Freger et al. |
| 7,162,922 B2 | 1/2007 | Freger et al. |
| 7,181,955 B2 * | 2/2007 | Gysling ................. G01F 1/668 73/53.03 |
| 7,216,536 B2 | 5/2007 | Young et al. |
| 7,275,421 B2 * | 10/2007 | Gysling ................ G01F 1/7084 73/597 |
| 7,389,187 B2 * | 6/2008 | Kersey .................... G01F 1/662 702/45 |
| 7,400,985 B2 * | 7/2008 | Fernald ................... G01F 1/666 702/45 |
| 7,469,033 B2 | 12/2008 | Kulik et al. |
| 7,481,106 B2 | 1/2009 | Raykhman et al. |
| 8,174,258 B2 | 5/2012 | Raykhman et al. |
| 2003/0079553 A1 | 5/2003 | Cain et al. |
| 2003/0089161 A1 | 5/2003 | Gysling |
| 2003/0230150 A1 | 12/2003 | Drahm et al. |
| 2004/0060345 A1 | 4/2004 | Eggen et al. |
| 2004/0173021 A1 | 9/2004 | Lizon et al. |
| 2004/0181359 A1 | 9/2004 | Freger et al. |
| 2005/0178198 A1 | 8/2005 | Freger et al. |
| 2005/0224279 A1 | 10/2005 | Gilmer et al. |
| 2007/0062260 A1 | 3/2007 | Wenger et al. |
| 2007/0068248 A1 | 3/2007 | Freger et al. |
| 2008/0257036 A1 | 10/2008 | Chaudoreille et al. |
| 2008/0307888 A1 | 12/2008 | Yoshioka et al. |
| 2009/0084178 A1 | 4/2009 | Sinha |
| 2010/0011882 A1 | 1/2010 | Gebhardt et al. |
| 2012/0222471 A1 * | 9/2012 | Raykhman ......... G01N 29/4472 73/64.53 |

FOREIGN PATENT DOCUMENTS

| | | |
|---|---|---|
| CN | 100445703 C | 12/2008 |
| EP | 1601936 A2 | 12/2005 |
| EP | 1709149 A2 | 10/2006 |
| JP | 01-311250 A | 12/1989 |
| JP | H11248514 A | 9/1999 |
| RU | 2194977 C2 | 12/2002 |
| WO | 2004074782 A2 | 9/2004 |
| WO | 2005062945 A2 | 7/2005 |

OTHER PUBLICATIONS

Webpages for "VBS Series" from www.stiautomaticproducts.com.
Webpages from www.astronet.ru including excerpt from on-line article "Earth's Crust Resesarch: Geophysical Methods" and concise explanation of relevance in English.
Webpages from www.hitech.com including excerpt of on-line article "Penetrating Pulse Technology".
Webpages with "VisselCheck ST" marketing materials, from www.canongatechnology.co.uk.
Cover and excerpt from The Theory of Sound by John William Strutt, Baron Rayleigh, vol. I, Second Edition, Dover Publications, pp. 180, 181, 246, 247.
Cover, and excerpt from Marks' Standard Handbook for Mechanical Engineers, 10th Edition, by Eugene A. Avallone and Theodore Baumeister III, McGraw-Hill,pp. 12-117.
Cover, Forward, and excerpts from B. M. Yavorsky and A.A. Detlaf, Physics Handbook, 3.sup.rd edition, M. Nauka, 1990 and concise explanation of relevance in English.
Sontag, Eduardo D., "Mathematical Control Theory: Deterministic Finite Dimensional Systems", Second Edition, Texts in Applied Mathematics/6, 1998.
Viscosity: http://hypertextbook.com/physics/matter/viscosity/.

* cited by examiner s   - Content velocity
L   - Content level in the conduit
$\rho$   - Density of the content
$\mu$   - Dynamic viscosity of the content
$\nu$   - Kinematic viscosity of the content
$Q_V$ - Volumetric flow rate
Qm - Mass flow rate
A   - Cross section area occupied by the content
l   - Length of the conduit's segment between supports 1. Ultrasound Level Meter
2. Conduit's Cross Section Area Occupied by Content Material
3. Nuclear Density Meter
4. Heater & 1st Temperature Sensor
5. 2nd Temperature Sensor
6. Velocity Analyzer & Calculator
7. Content Material Velocity Meter 3. Striker - Receiver Module
4. Remote Receiver of Content Material Spherical Wave (Longitudinal Propagation)
5. Data Processing Module
6. Sensor Registry for Spherical Wave (Transverse Direction of Propagation)

METHOD AND APPARATUS FOR NON-INVASIVELY MEASURING PHYSICAL PROPERTIES OF MATERIALS IN A CONDUIT

CROSS-REFERENCE TO RELATED APPLICATIONS

This application claims the benefit of and priority under 35 U.S.C. §119(e) to U.S. Provisional Patent Application Ser. No. 61/930,611 filed Jan. 23, 2014, which is hereby incorporated herein by reference in its entirety.

BACKGROUND

Field of the Invention

Aspects of the present invention relate to systems and methods for non-invasively measuring physical properties of materials in a conduit and for measuring physical properties associated with materials flowing through a conduit.

Discussion of Related Art

The measurement of one or more physical properties of immobile or flowing materials is an indispensable part of many technological processes spanning a wide variety of industries that include, for example, chemical, pharmaceutical, petro and oil, food, building materials, and waste water. Density, viscosity, volumetric flow rate, and mass flow rate are physical properties of free-flowing materials that are considered challenging for non-invasive measurement. As used herein, the term free-flowing material refers to liquids, loose solids, and their combination, e.g., slurries.

Non-invasive measurement of the physical properties of materials within a confined area has been conventionally performed by inspecting the material using one of several approaches. The inspection techniques employed may be radiometric, gravitational, electromagnetic, optical or ultrasound-based in nature. Radiation-based methods monitor attenuation of radioactive energy passing through a container's walls and the material contained within. Unfortunately, radiation-based methods suffer from a number of disadvantages. For instance, density is typically a prime focus of such methods because radiation-based methods are generally not applicable to measurement of shear resistance-relating variables such as viscosity of liquids, coalescence of solid particles, or material flow rates. Further, acquiring a license for the use of portable radiation-based density measurement devices may be burdensome and time consuming in certain jurisdictions and may require certified personnel to be trained and certified. Moreover, these systems may perform with reduced accuracy for certain density ranges, such as those associated with light powder materials in the range from 20 to 150 g/L. Additionally, radiation-based systems may require special design and operational effort to maintain a sufficient degree of safety and security.

Gravitational systems for measuring the density of non-gaseous materials require adjustment to account for the empty vessel's weight and internal dimensions. Gravitation systems are limited in their applicability due to the problems with installation of the weight-measuring equipment which frequently utilize various load cell arrangements. In addition, weight-measuring systems are not applicable to viscosity measurement.

Optical methods are applicable to measuring density of materials in vessels equipped with an aperture for focusing an optical beam through the filling material. Optical, non-invasive methods for density measurement may have limited use due to transparency requirements placed on the material to be measured.

The propagation of ultrasound waves through a material may also be used to measure one or more physical properties of materials. Ultrasound-based methods demonstrate the ability to discriminate between various physical properties of the material. If applied to liquids, these methods allow measurement of density or viscosity. However, conventional measuring methods that utilize ultrasound waves suffer from several disadvantages.

For example, ultrasound-based methods require a substantial amount of homogeneity of the filling material when used for density or viscosity measurements. Thus, ultrasound-based technologies are not applicable to loose solids and heterogeneous liquids like mud, suspensions, pulp or slurry. The presence in a vessel of various kinds of agitating members, mixers or bubblers can produce a similar effect on the accuracy of density or viscosity measurement. In addition, these methods require an ultrasound emitter/receiver attachment to the vessel wall. These attachments may require special treatment of the container's surface in order to create a conduit for ultrasound waves emitting by a transducer into the container. Moreover, ultrasound-based methods are highly sensitive to disturbances affecting the speed of sound in the medium, e.g., temperature and flow variations. Thus, special compensation techniques are conventionally employed to provide for the invariance of the output variables to these disturbances. Also, the amount of power consumed by an ultrasound transducer in providing a sufficient pulsation could limit the applicability of these methods.

The measurement of other physical properties, including flow rates such as volumetric and mass flow rates, of a material may be performed by a wide variety of devices. For example, coriolis meters may measure the mass and volumetric flow rate of a material and vortex flow meters may measure the volumetric flow. Some devices may utilize an invasive technique for determining flow rates, such as mechanical devices that include a rotating member for measuring the speed of the moving material. Other devices may utilize a non-invasive technique for determining flow rates, such as volumetric flow meters that use the Doppler Effect of ultrasound waves, or flow meters that utilize ultrasound waves generated by the friction between moving material and the inner surface of the pipe.

SUMMARY OF INVENTION

In at least one embodiment, an apparatus for measuring one or more physical properties of a material flowing through a conduit is provided. The apparatus includes a striker configured to initiate a vibration on a wall of the conduit at a first location; a first sensor configured to capture a response to the vibration at the first location; a second sensor configured to capture a response to the vibration at a second location, the second location disposed along a length of the conduit in a direction of the flow of the material through the conduit; and an analyzer configured to determine a velocity of the material based on the captured response at the first location and the second location.

In the apparatus, the first sensor may be configured to detect spherical compression longitudinal waves generated by the striker in a direction normal to the length of the conduit. The second sensor may be configured to detect spherical compression longitudinal waves generated by the striker and carried by the material in the direction of the flow of the material through the conduit. The apparatus may further include a plurality of sensors positioned around a perimeter of the conduit at the first location and configured to capture at least one response to the vibration.

In the apparatus, the analyzer may be further configured to determine a dynamic viscosity based on the at least one captured response from the perimeter of the conduit. The analyzer may be further configured to determine a volumetric flow rate of the material based on the velocity of the material. The analyzer may be further configured to determine a mass flow rate of the material based on the captured responses at the first location and the second location.

The apparatus may further include a level meter configured to determine the level of the material flowing through the conduit. In the apparatus, the analyzer may be further configured to determine a density of the material based on the level of the material and determine a kinematic viscosity based on the density. The conduit may be at least one of partially filled with material or open. The material may be a heterogeneous liquid.

In another embodiment, a method for measuring one or more physical properties of a material flowing through a conduit is provided. The method includes acts of initiating a vibration on a wall of the conduit at a first location; capturing a response to the vibration at the first location; capturing a response to the vibration at a second location disposed along a length of the conduit in a direction of the flow of the material through the conduit; and determining a velocity of the material based on the captured responses at the first location and the second location.

The method may further include an act of capturing a response to the vibration at the first location at one or more positions around a perimeter of the conduit. The method may further include an act of determining a dynamic viscosity of the material based on the captured response at the one or more positions along the perimeter. The method may further include an act of determining a volumetric flow rate of the material based on the velocity of the material. The method may further include an act of determining a mass flow rate of the material based on the captured responses at the first location and the second location. In the method, the velocity may be determined using at least one of a system of equations and a mathematical formula.

The conduit may be partially filled with the material and the method may further include acts of determining a level of material in the conduit and determining a density of the material based on the level of the material and the captured response at the first location. The method may further include an act of determining a mass flow rate based on the density and the velocity. The method may further include an act of determining a kinematic viscosity based on the density.

Still other aspects, examples, and advantages of these exemplary aspects and examples, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment in any manner consistent with at least one of the objects, aims, and needs disclosed herein, and references to "an embodiment," "some embodiments," "an alternate embodiment," "various embodiments," "various embodiments," "certain embodiments," "one embodiment," "at least one embodiment," "this and other embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of the invention. The drawings, together with the remainder of the specification, serve to explain principles and operations of the described and claimed aspects and examples. In the figures, each identical or nearly identical component that is illustrated in various figures may be represented by a like numeral. For purposes of clarity, not every component may be labeled in every figure. In the figures:

DETAILED DESCRIPTION

Figure 1:
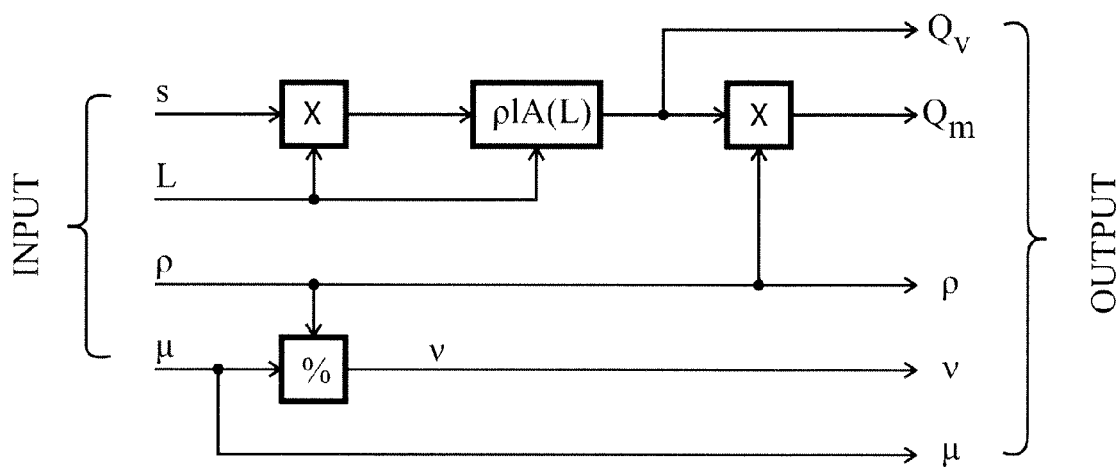
FIG. 1 is an informational block diagram describing the relationship of various variables used for determining one or more physical properties.

In many industrial processes there exists a need to non-invasively and continuously monitor one or more physical properties of a material flowing through a conduit. Continuous measurement may be desirable for processes that run on a round-the-clock schedule. Invasive techniques may require shutting down the process, which interrupts the production cycle. Current measurement methods, such as those described above, may use one or more separate devices to obtain each different type of measurement. There exists a need for a device that can consolidate one or more of these measurements into a minimum number of devices.

Aspects and examples disclosed herein are directed toward simultaneous non-invasive measurement of one or more physical properties of a material flowing through a conduit. Certain examples utilize a percussion-based method for measuring certain physical properties. The percussion-based method may be used with one or more other types of techniques, such as ultrasound, to determine other physical properties, such as flow rates. Various sensors may be placed on a conduit and at one or more positions along the fluid flow path. These sensors may be used in combination with one or more of the measurement techniques in determining physical properties associated with a material flowing through a conduit. The disclosed systems may be used for open or closed conduits, and for conduits that are completely filled with material, or only partially-filled.

The disclosed systems and methods are capable of non-invasively and simultaneously determining physical properties such as velocity, density, kinematic viscosity, dynamic viscosity, volumetric flow rates, and mass flow rates for materials flowing through a conduit. In one example, a striker-receiver module (SRM) includes a striker that initiates a vibration on the wall of the conduit to create one or more oscillatory responses that may be vibration or mechanical wave-type responses. The SRM is used in combination with several sensors that detect the mechanical waves as they are transmitted through the material. The material's physical properties, including the speed at which the material is flowing through the conduit, affect the energy of the waves detected by the sensors. In at least one example, the system also includes a level meter, such as an ultrasound level meter, that is used to determine the amount, or level, of material present in the conduit. One or more of these pieces of information are directed to a data processing module, otherwise referred to herein as an analyzer, that then uses one or more of the measured properties to calculate other unknown properties. One or more of these properties may be reported or otherwise used to determine process performance.

According to one embodiment, one or more physical properties, such as the density, viscosity, and velocity may be determined for a fluid flowing through a conduit, such as a pipe. According to some embodiments, the material may completely fill the conduit. In other examples, the material may only partially fill the conduit. In one or more embodiments, an apparatus may execute a method for determining one or more physical properties of the material flowing through the conduit. According to one example, the apparatus may include a striker, a first and a second vibration sensor, a receiver, and a controller. While executing an example method, the apparatus may determine one or more physical properties by populating a system of equations with empirical data and then solving the system of equations. In other examples, the apparatus may use one or more formulas for determining the physical properties of the material.

The systems and method disclosed herein may offer several advantages over existing systems and methods. For example, the number of separate devices or elements needed to determine several physical properties, including density, viscosity, the level or height of a material present in a conduit, the velocity of the flow of material directed along the conduit, the volumetric flow rate, and the mass flow rate, may be reduced when compared to other systems capable of measuring the same number and variety of physical properties. Having a smaller footprint is especially useful for applications having minimal or densely populated space, such as oil rigs or platforms. Obtaining the physical measurements is also independent of the composition of the material, meaning that a wider variety of materials of varying compositions may be measured. As described above, various embodiments implement non-invasive systems and methods. In some embodiments, the non-invasive systems and methods provide for no direct physical contact between the measurement apparatus and the material of interest. In other embodiments, the non-invasive systems and methods provide for no direct physical contact between the measurement apparatus and the material of interest that would inhibit the functionality of one or more processes associated with the material. Further, the system is capable of determining physical properties of homogeneous and heterogeneous materials flowing through a conduit of any cross-sectional geometry, including open conduits and partially-filled conduits. The system may also be economical to install and use and is capable of being used in a retrofit type of application.

The aspects disclosed herein in accordance with the present invention are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments or examples are not intended to be excluded from a similar role in any other embodiments or examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

One or more example methods and apparatuses disclosed herein are based on non-invasively determining one or more physical properties of a material disposed in a conduit. As used herein, the term "physical property" refers to one or more measureable properties of a material and is intended to include flow rates or other system properties associated with the material. Non-limiting examples of physical properties include density, viscosity, including dynamic and kinematic viscosity, composition, such as the percentage of solid particles in a slurry, shear resistance, and specific gravity. Physical properties of a flowing material may also include a velocity and one or more flow rates of a material flow, including a volumetric flow rate and a mass flow rate. Other system properties associated with a physical property may include the presence of a material, the level of a material, level deviation, and the like.

In some instances, a physical property of a material may be capable of being measured directly or indirectly. In other instances, a physical property may be calculated using one or more mathematical relationships. For example, FIG. 1 illustrates an informational block diagram describing the relationship of various variables used for determining one or more physical properties of a material flowing through a conduit. Input data, including material velocity (s), the level of the material in the conduit (L), the bulk density of the material (ρ), and the dynamic viscosity of the material (μ), may all be included to simultaneously determine one or more output variables, including the volumetric flow rate of the material ($Q_v$), the mass flow rate of the material ($Q_m$), and the kinematic viscosity of the material (v). One or more of the variables may be measured by an apparatus associated with the material and conduit. One or more measurement technologies may be associated with each apparatus. In certain instances, a user may input a value associated with a variable.

The block diagram illustrated in FIG. 1 indicates that the one or more input variables may support the vector-output $\{Q_v, Q_m, \rho, v, \mu\}$. For example, kinematic viscosity (v) is a function of dynamic viscosity (μ) and density (ρ), and the mass flow rate ($Q_m$) is a function of density (ρ) and material velocity (s). Further, a separate relationship shown in the diagram uses other properties, including the length of the conduit's segment between supports (l), and the cross-sectional area occupied by the material in the conduit (A(L)), to determine properties such as the volumetric flow rate of the material ($Q_v$) and the mass flow rate of the material ($Q_m$).

Figure 2:
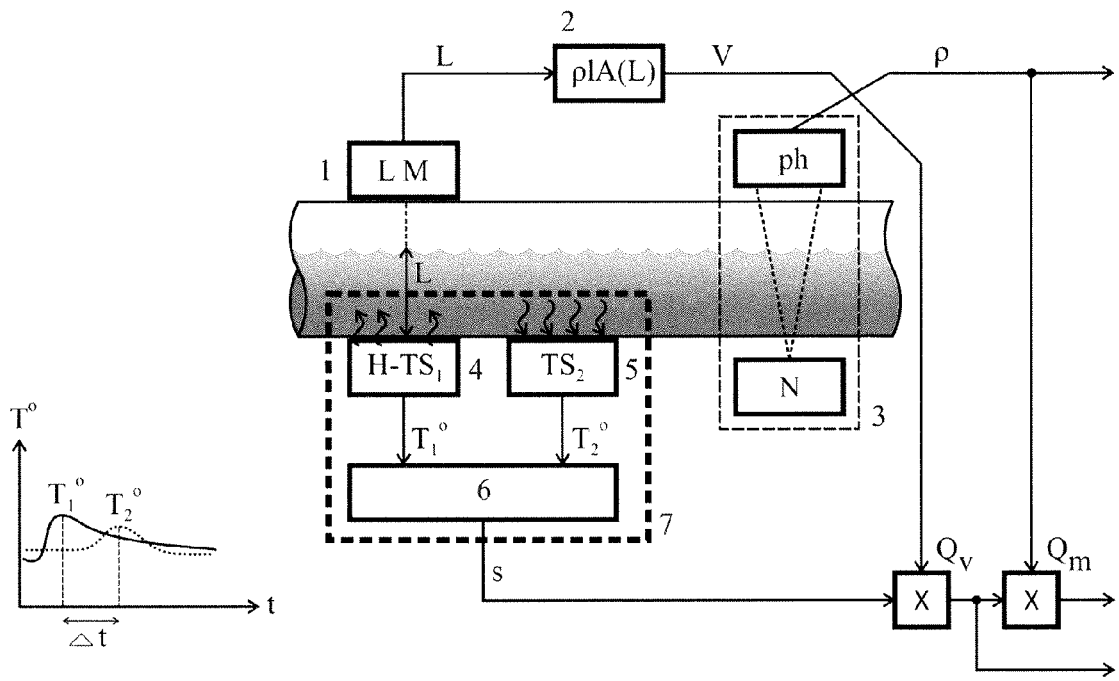
FIG. 2 is a functional block diagram of an installation for determining one or more physical properties of a fluid flowing through a conduit using several measurement techniques.

FIG. 2 illustrates a functional block diagram of an installation for determining one or more physical properties of a fluid flowing through a conduit. For purposes of this example, the conduit is considered to be partially-filled by the material. The illustrated system includes four major functional blocks, including an ultrasound level meter 1, a cross-sectional area amplifier 2, a nucleonic density meter 3, and a content material velocity meter 7. Also included in the system is a heater/first temperature sensor 4, a second temperature sensor 5, and a velocity analyzer and calculator 6. The content material velocity meter 7 is configured to be based on the analysis of the transfer time of the heat gradient originating at a first location point on the outer surface of the conduit and subsequently captured at a second location point on the outer surface of the conduit downstream from the first location point. Part of the system is configured to determine flow rates based on monitoring the thermal gradient of material along the conduit. The measurement for the mass flow rate $Q_m$ of material flowing through the conduit is aided by the use of the nucleonic density meter 3.

The system illustrated in FIG. 2 is based on three different measurement technologies. For example, an acoustic gauge is used in association with the level meter 1, and nuclear radiation is used in association with the density meter 3. In addition, a thermal energy gradient is used to establish the flow rate for the material in the conduit. To obtain viscosity measurements, an additional viscometer would need to be positioned into the system.

Figure 3:
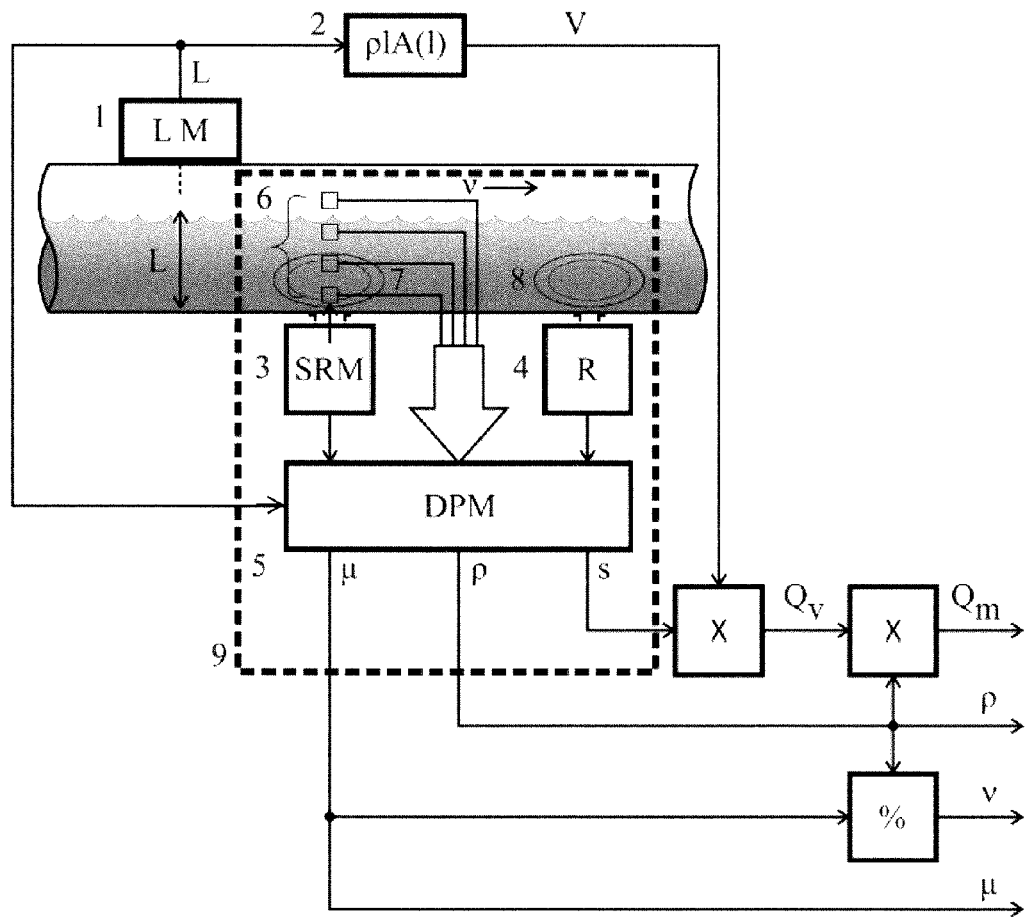
FIG. 3 is a functional block diagram of an installation for determining one or more physical properties of a fluid flowing through a conduit using a percussion-based non-invasive measurement technique.

FIG. 3 illustrates a functional block diagram of an installation for non-invasively determining one or more physical properties of a fluid flowing through a conduit. Included in the system is an ultrasound level meter 1 and a cross-sectional area amplifier 2. In contrast to the system depicted in FIG. 2, the system includes a striker-receiver module (SRM) 3 that applies a temporal mechanical load to the outer wall of the conduit and monitors the oscillatory motion of the outer wall. The SRM works in combination with a registry of vibration sensors 6 that are positioned on the outer lateral surface of the wall of the conduit and a vibration sensor-receiver (R) 4 that is positioned downstream from the SRM. The registry of vibration sensors 6 is configured to detect vibrations produced by mechanical waves transversely propagating through the content material of the conduit. The vibration sensor 4 is configured to detect vibrations produced by mechanical waves that originate in the content material in the vicinity of the SRM, propagate longitudinally and are additionally carried by the flow of material. For example, waves propagating within the material generated by the SRM are represented by 7 and waves propagating within the material generated by the SRM and carried down the conduit by the flow of the material are represented by 8. The sensor-receiver 4 is thus configured to detect the longitudinal propagation of spherical compression longitudinal (sound) waves generated by the SRM and carried down the conduit by the material. The system also includes an analyzer, such as a data processing module (DPM) 5 that functions to calculate one or more physical properties of the material flowing through the conduit, such as the density, kinematic viscosity, dynamic viscosity, volumetric flow rate, and mass flow rate based on the data obtained by one or more other components of the system, including the SRM 3, the sensors 6, and the sensor-receiver 4.

The functional block 9 represents the system of devices that simultaneously measure the material's velocity, density, and viscosity obtained by the application of a percussion method of measurement, which is explained in further detail below. In general terms, during operation the temporal mechanical load applied to the outer wall of the conduit by the SRM results in the generation of several types of vibration responses. The macro-oscillation of the body of the conduit between the conduit's mechanical supports is used to measure the bulk density of the material in the conduit, and the spherical compression longitudinal waves propagating through the material in a normal direction are used to obtain measurements of the content's viscosity. Transfer of these waves in the direction of the flow of material may be used to determine the material's velocity. The material's volumetric and mass flow rates may then be calculated according to the following formulas:

$$\text{Volumetric Flow Rate} = \text{Material Velocity} \times \text{Material Level} \quad (1)$$

$$\text{Mass Flow Rate} = \text{Material Bulk Density} \times \text{Volumetric Flow Rate} \quad (2)$$

The apparatus and method(s) illustrated in FIG. 3 requires only two measurement technologies and is capable of determining a wide range of physical properties. For example, the SRM and its components in the illustrated example are configured to determine at least five different physical properties, including viscosity. Further, the system does not require the use of nuclear radiation for determining density, nor does it require the use of a thermal energy gradient.

Figure 4:
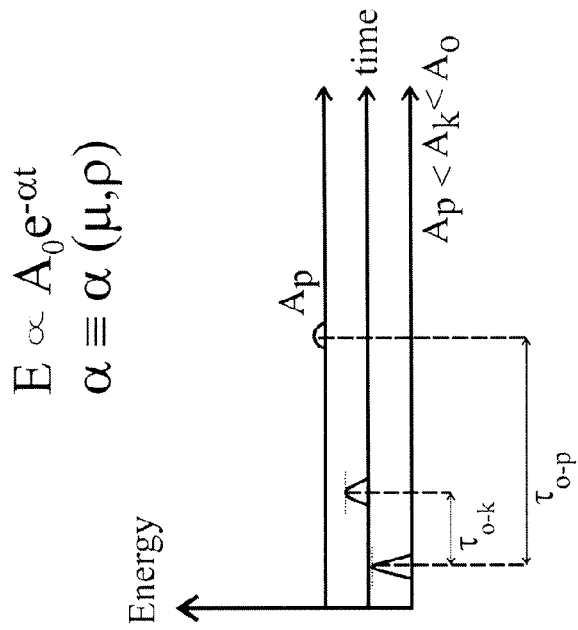
FIG. 4 is a schematic diagram providing an explanation of a principle of operation of determining one or more physical properties of a fluid in a partially-filled conduit.
Figure 4:
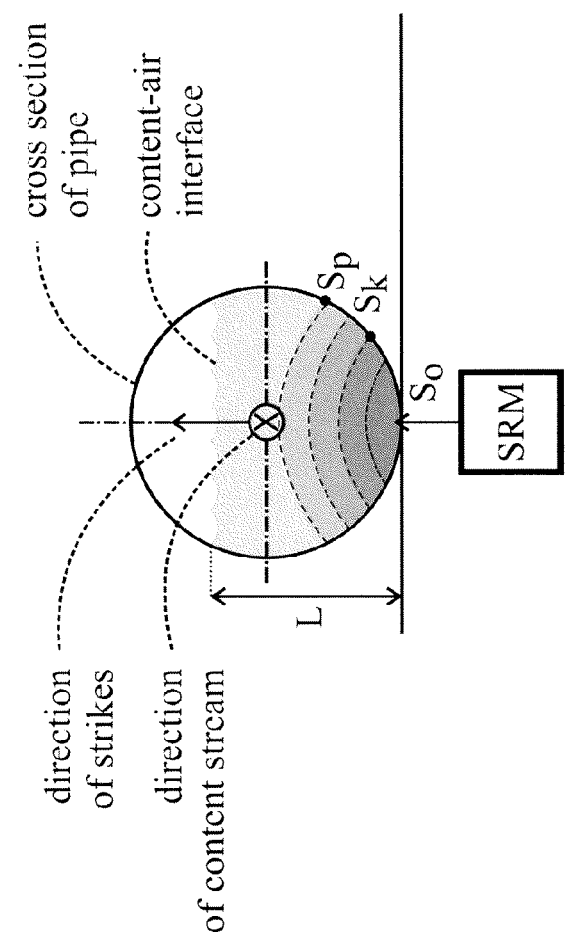

Viscosity, density, and velocity measurements obtained using the system illustrated in FIG. 3 are determined by the placement of one or more vibration sensors positioned at predetermined locations on the outer surface of the conduit along the cross-sectional circumference of the conduit. The principles behind at least some of the underlying calculations, including dynamic viscosity, are illustrated in FIG. 4 and are based in part on a percussion method for determining physical properties of a material within a conduit. As shown in FIG. 4, several vibration sensors $S_o$, $S_k$, and $S_p$, are positioned along the exterior of the conduit. For example, $S_o$ is placed near the bottom of the conduit, and $S_k$ and $S_p$ are placed further upward. In some instances, the vibration sensors are arranged in a predetermined pattern. For example, the vibration sensors may be placed at equal distances from each other. According to some examples, the vibration sensors may be placed to form a plane through the center of the conduit. The SRM includes a striker, which strikes against some point on the conduit. The vibration sensors $S_0$, $S_k$, and $S_p$ detect the resulting spherical compression longitudinal waves transmitted in the transverse direction and report this information back to the data processing module. The time-dependent decaying energy of these waves as they travel through the material signifies several properties about the material present in the conduit. For example, the faster the energy decay, the higher the viscosity value of the material.

Figure 9:
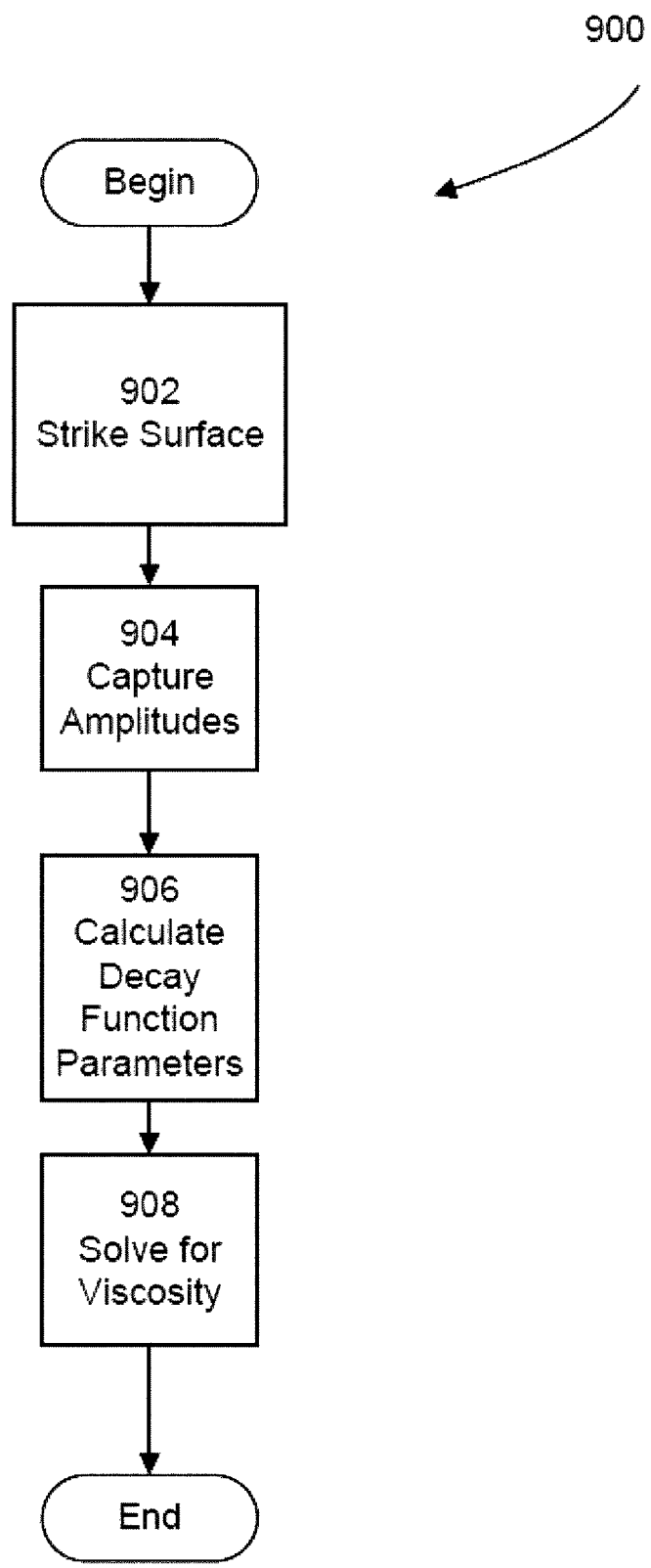
FIG. 9 is a flowchart of one or more methods in accordance with one or more aspects of the disclosure.

FIG. 9 illustrates one example of a measurement process 900 for determining a viscosity value of a material within a conduit. In some embodiments, the measurement process 900 is executed by a system of devices, such as the system 9 described above with reference to FIG. 3. In broad overview, the measurement process 900 determines the viscosity value by initiating a mechanical load on a surface of the conduit and measuring one or more amplitudes of one or more resulting waves at various times and locations along the surface of the conduit.

The measurement process 900 begins at act 902, where a striker applies a mechanical load to a surface of a conduit. The striker may be included in, for example, the SRM described above with reference to FIG. 4. In act 904, a plurality of vibration sensors detect amplitudes of resulting spherical compression longitudinal waves. The vibration sensors may include, for example, the $S_0$, $S_k$, and $S_p$ vibration sensors described above with reference to FIG. 4. In act 906, an analyzer processes the detected amplitudes and detection times to determine parameters of a decay function, such as the decay function illustrated in FIG. 4. The analyzer may include, for example, the data processing module described above with reference to FIG. 4. In act 908, the analyzer solves the decay function for the viscosity value and the measurement process 900 ends.

Processes in accord with the measurement process 900 enable measurement systems to quickly, reliably, and non-invasively determine the viscosity of a material using a plurality of vibration sensors in contact with a surface of a conduit.

One or more of the measurement principles disclosed herein may also be explained in PCT Application No. PCT/US10/44292, titled METHOD AND APPARATUS FOR MEASUREMENT OF PHYSICAL PROPERTIES OF FREE FLOWING MATERIALS IN VESSELS, filed Aug. 3, 2010, PCT Application No. PCT/US2014/015174, titled NON-INVASIVE METHOD FOR MEASUREMENT OF PHYSICAL PROPERTIES OF FREE FLOWING MATERIALS IN VESSELS, filed Feb. 6, 2014, U.S. Pat. No. 7,162,922, titled NON-INVASIVE METHOD FOR DETECTING AND MEASURING FILLING MATERIAL IN VESSELS, filed Dec. 23, 2004, and U.S. Pat. No. 7,103,500, titled APPARATUS AND METHOD FOR DISTANCE MEASUREMENT WITH CONTROLLED MODULATION OF EMITTED PULSES, filed Feb. 11, 2004, each of which is hereby incorporated herein by reference in their entirety, and owned by the same owner as the instant application.

Figure 5:
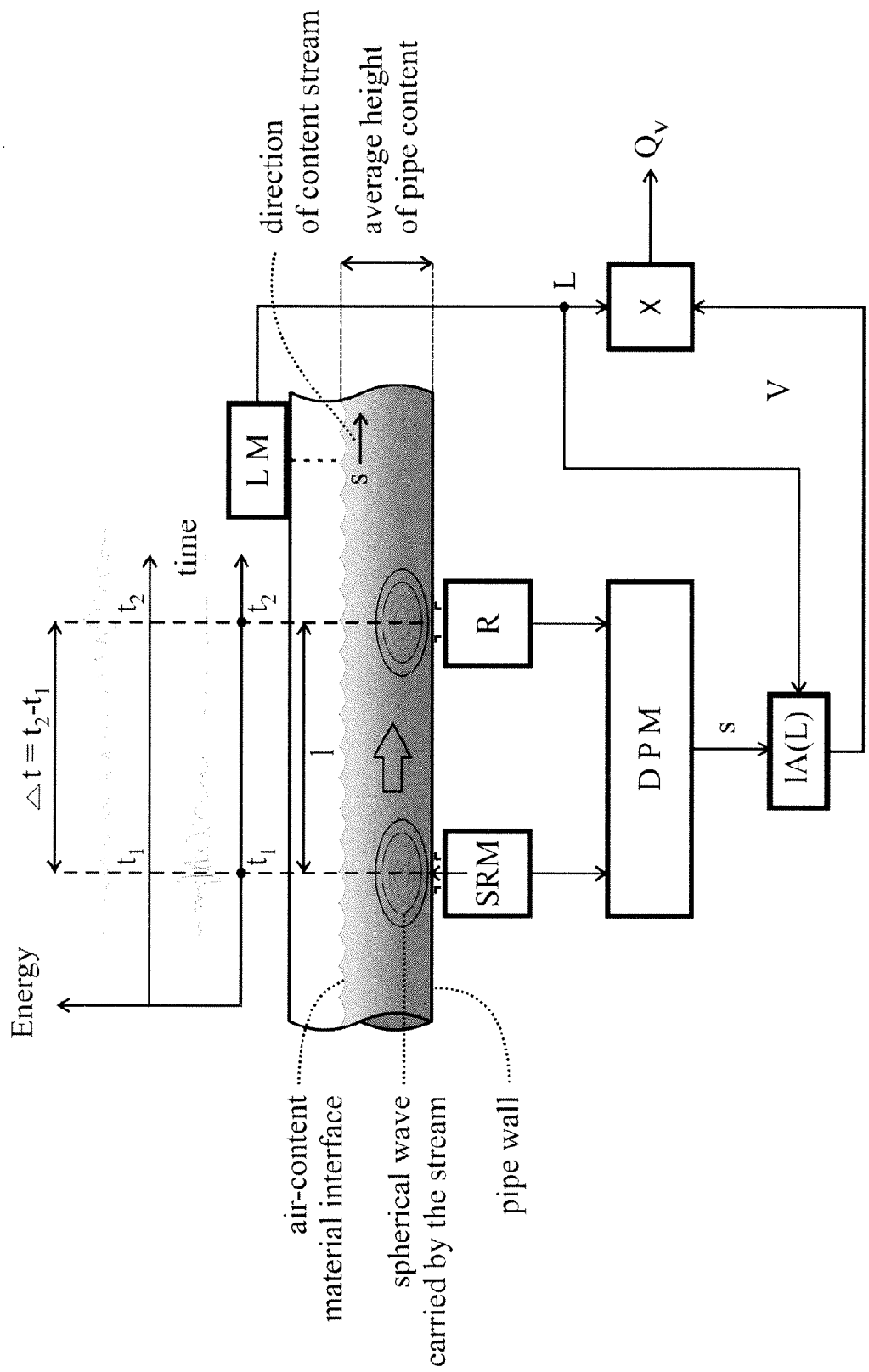
FIG. 5 is a block diagram providing an explanation of a principle of operation of determining a stream velocity and a flow rate of a fluid in a partially-filled conduit.

The placement of the vibration sensor-receiver R downstream from the SRM as illustrated in FIG. 3 allows for the system to determine the material's velocity. The underlying principles behind these calculations are illustrated in FIG. 5. For example, the sensor-receiver R is positioned at a predetermined distance on the outer surface of the conduit in the direction of the flow of material. The same strike force initiated in the discussion related to FIG. 4 applies in FIG. 5. However, instead of detecting spherical compression longitudinal waves generated by the striker in direction normal to the length of the conduit, the system detects the waves generated by the striker as they move through the material in the direction of flow and captured by the additional sensor-receiver R. The system also includes the use of the ultrasound level meter (LM) to non-invasively determine the level of material present in the conduit.

Figure 10:
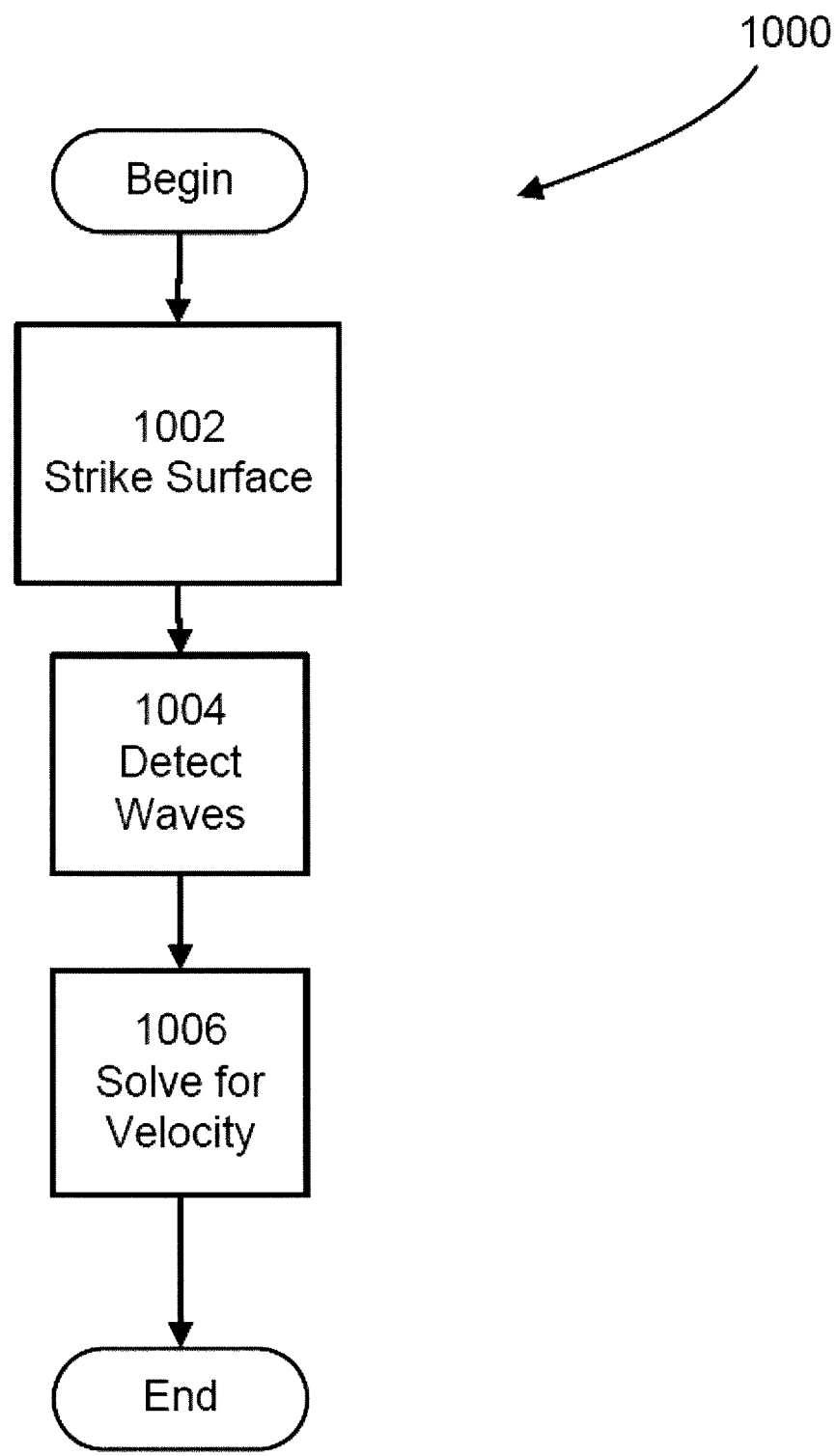
FIG. 10 is a flowchart of one or more methods in accordance with one or more aspects of the disclosure.

FIG. 10 illustrates one example of a velocity measurement process 1000 for determining a velocity value of a material within a conduit. In some embodiments, the velocity measurement process 1000 is executed by a system of devices, such as the system 9 described above with reference to FIG. 3. In broad overview, the velocity measurement process 1000 determines the velocity value of the material by initiating a mechanical load on a surface of the conduit and detecting the presence of one or more resulting waves at various times and locations along a surface of the conduit.

The measurement process 1000 begins at act 1002, where a striker applies a mechanical load to a surface of a conduit. The striker may be included in, for example, the SRM described above with reference to FIG. 5. In act 1004, a plurality of vibration sensors detects the presence of a resulting spherical compression longitudinal wave within the material at a plurality of locations. The plurality of vibration sensors may include, for example, the vibration sensor included in the SRM and the sensor-receiver R described above with reference to FIG. 5. In act 1006, an analyzer determines a velocity value for the wave by dividing the distance between the locations of two vibration sensors of the plurality of vibration sensors by the difference in the times of when the wave was detected at the locations. Next, the analyzer determines the velocity value of the material by subtracting a reference velocity value (e.g., a velocity with which a wave would propagate through the material if the material were stationary) from the velocity value of the wave and the measurement process 1000 ends.

Processes in accord with the measurement process 1000 enable measurement systems to quickly, reliably, and non-invasively determine the velocity of a material using a plurality of vibration sensors in contact with a surface of a conduit.

The system illustrated in FIG. 3 is capable of determining one or more physical properties for a wide variety of materials, including liquids, loose solids such as powder materials, and slurries. In certain instances, the concentration of the solids in the material may be higher than 50%. The system is also capable of measuring flow rates in laminar flow applications and is capable of performing under a wide range of temperatures. For example, the system may be capable of handling process temperatures up to 250° C. and ambient temperatures as low as −40° C. Further, the systems and methods may be applied to applications having open, close, filled, or partially-filled conduits. The system may also be configured to determine one or more physical properties continuously, allowing for the capability to provide real-time process control.

Figure 6:
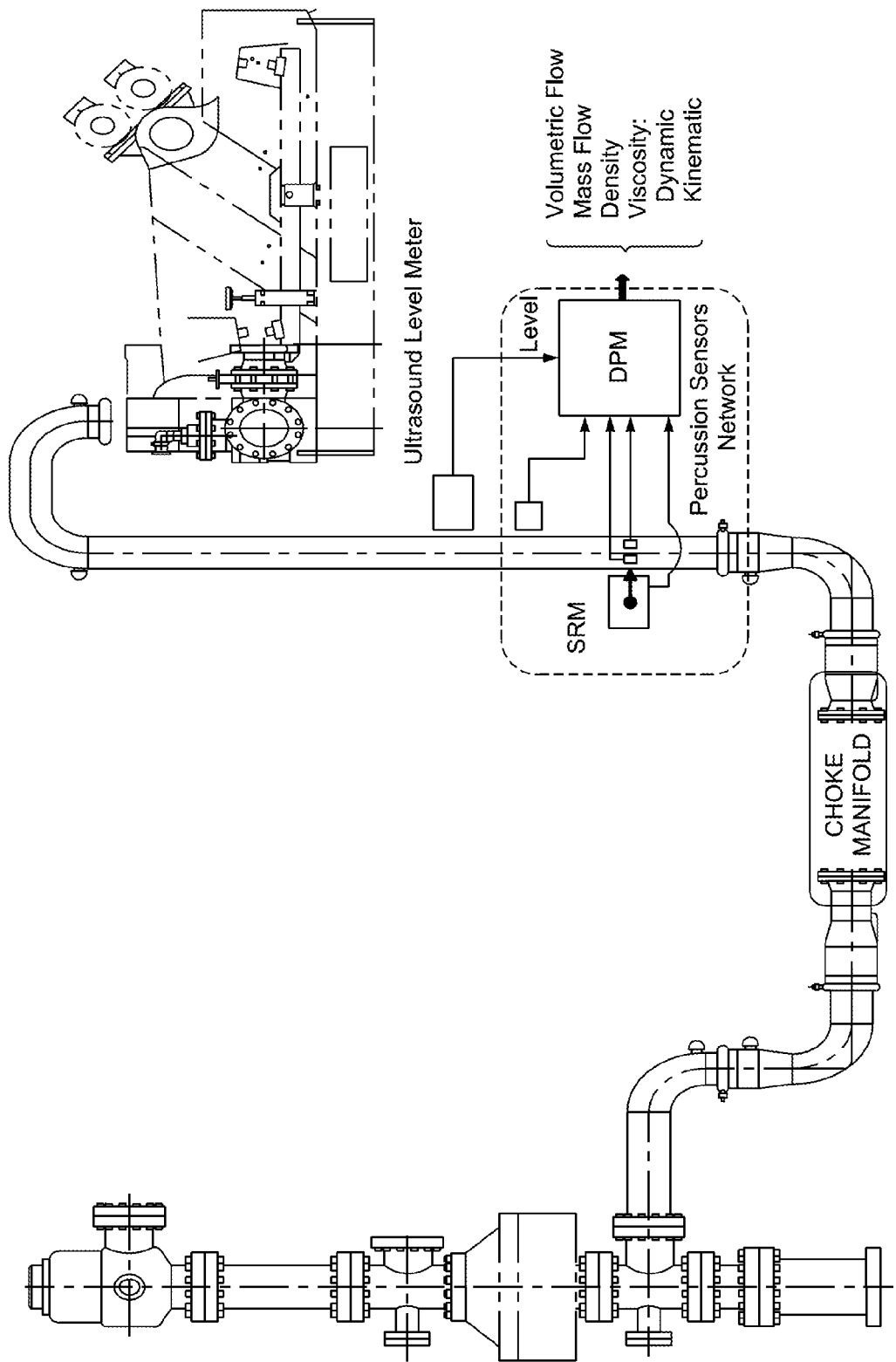
FIG. 6 is a functional diagram of an exemplary installation of a measurement system in an oil drilling application.

Illustrated in FIG. 6 is an example of the disclosed system used in an oil drilling application. One or more components of the embodiment illustrated in FIG. 3 may be applied to a conduit carrying oil or other fluids associated with an oil drilling or refining process. As illustrated in FIG. 6, the system is positioned on a vertical section of pipe, but is also capable of being placed on horizontal or inclined sections of pipe. The disclosed system may be ideal for such an application due to its small footprint and ability to determine physical properties of a wide variety of materials. For example, the disclosed system may be positioned at one or more locations on the oil rigging apparatus, and may be used to determine flow rates, density, and viscosities of the materials contained in the rig's conduits.

The measurement system featured in FIG. 6 is capable of replacing and offering advantages over one or more other existing technologies that could be used to determine properties associated with the flowing materials. For example, the combination of an ultrasound flow meter and a microwave density meter is capable of determining flow rates and other system properties, but one or more additional devices are required. In contrast, the disclosed system is capable of offering the same information at a lower cost, with less equipment and non-invasively. A coriolis meter may also be used to determine flow rates and other properties, but these systems are invasive, expensive, can be quite large in size, and are difficult to install accurately.

Thus, aspects and embodiments provide a non-invasive measurement apparatus and method that is capable of determining one or more physical properties, including volumetric and mass flow rates, density, viscosity, material level, and concentration of solids in slurry for a filled or partially-filled conduit. The system is portable and has few moving parts and therefore requires minimum maintenance. The system is also not susceptible to clogs or leaks and is capable of measuring a wide variety of materials, including powder materials. Further, the system does not require a separate bypass line for performing various measurements and calculations, since the requisite measurements may be made using existing infrastructure. This increases accuracy and reduces installation costs.

Figure 7:
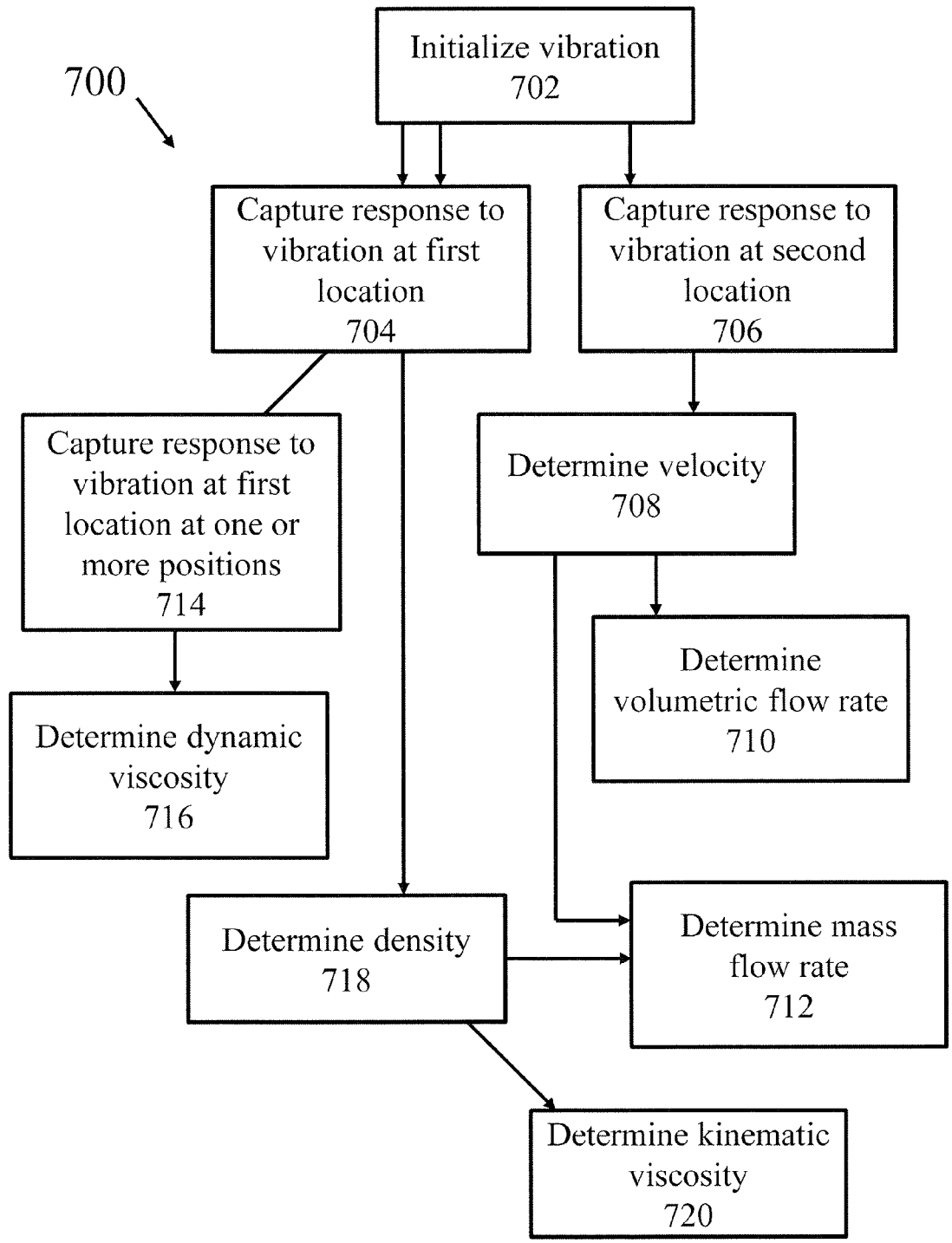
FIG. 7 is a flowchart of one or more methods in accordance with one or more aspects of the disclosure.

FIG. 7 is a process flow diagram illustrating at least one process, generally indicated at 700, that is in accordance with one or more aspects of the disclosure. In FIG. 7, step 702 includes initializing a vibration, for example, on a wall of the conduit at a first location. Step 704 includes capturing a response to the vibration at the first location and step 706 includes capturing a response to the vibration at a second location. For example, the second location may be disposed along a length of the conduit in a direction of the flow of material through the conduit. The velocity of the material is determined at step 708, for example, as described above in reference to FIGS. 5 and 10, based on the captured response at the first location and the second location. The velocity determined at step 708 may then be used to determine the volumetric flow rate at step 710. The process may also include capturing a response to the vibration at the first location at one or more positions at step 714, for example one or more positions around a perimeter of the conduit. These responses may be used to determine the dynamic viscosity at step 716, for example as described above in reference to FIGS. 4 and 9. Density may be determined at step 718, which may also require determining a level of the material in the conduit, and may also be based on the captured response at the first location. The density may be used in combination with the velocity determined at step 708 to determine the mass flow rate at step 712. The density determined at step 718 may also be used to determine the kinematic viscosity at step 720.

Figure 8:
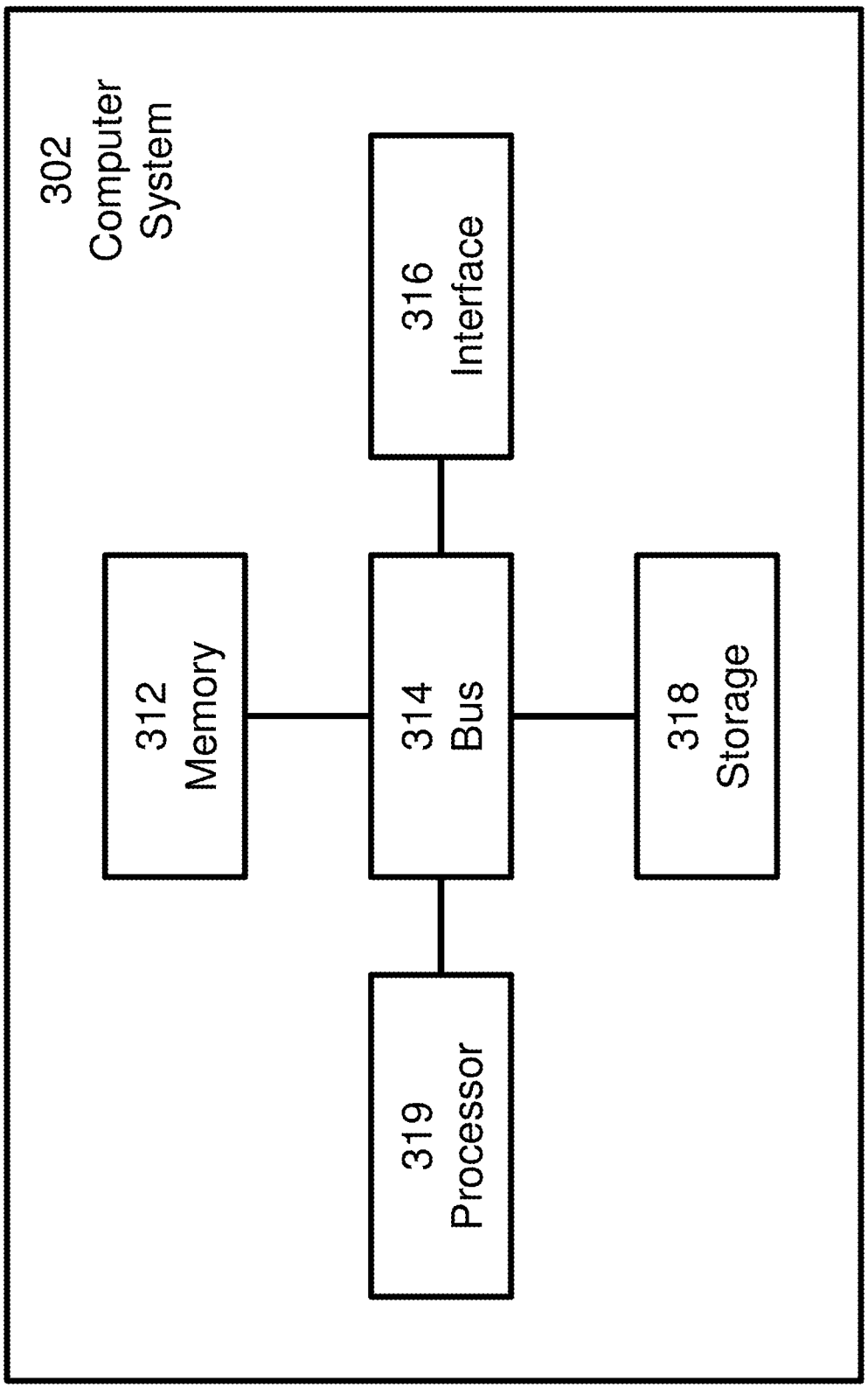
FIG. 8 is a block diagram of one example of a computer system that may be used to perform processes disclosed herein.

Referring to FIG. 8, there is illustrated a block diagram of a computer system 302, in which various aspects and functions disclosed herein may be practiced. The computer system 302 may include one more computer systems that exchange (i.e. send or receive) information. As shown, the computer system 302 may be interconnected by, and may exchange data through, a communication network. The network may include any communication network through which computer systems may exchange data. To exchange data using the network, the computer system 302 and the network may use various methods, protocols and standards, including, among others, Fibre Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST and Web Services. To ensure data transfer is secure, the computer system 302 may transmit data via the network using a variety of security measures including, for example, TSL, SSL or VPN. The network may include any medium and communication protocol.

FIG. 8 illustrates a particular example of a computer system 302. As illustrated in FIG. 8, the computer system 302 includes a processor 310, a memory 312, a bus 314, an interface 316 and data storage 318. The processor 310 may perform a series of instructions that result in manipulated data. The processor 310 may be a commercially available processor such as an Intel Xeon, Itanium, Core, Celeron, Pentium, AMD Opteron, Sun UltraSPARC, IBM Power5+, or IBM mainframe chip, but may be any type of processor, multiprocessor or controller. The processor 310 is connected to other system components, including one or more memory devices 312, by the bus 314.

The memory 312 may be used for storing programs and data during operation of the computer system 302. Thus, the memory 312 may be a relatively high performance, volatile, random access memory such as a dynamic random access memory (DRAM) or static memory (SRAM). However, the memory 312 may include any device for storing data, such as a disk drive or other non-volatile storage device. Various examples may organize the memory 312 into particularized and, in some cases, unique structures to perform the functions disclosed herein.

Components of the computer system 302 may be coupled by an interconnection element such as the bus 314. The bus 314 may include one or more physical busses, for example, busses between components that are integrated within a same machine, but may include any communication coupling between system elements including specialized or standard computing bus technologies such as IDE, SCSI, PCI and InfiniBand. Thus, the bus 314 enables communications, such as data and instructions, to be exchanged between system components of the computer system 302.

The computer system 302 also includes one or more interface devices 316 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 302 to exchange information and communicate with external entities, such as users and other systems.

The data storage 318 may include a computer readable and writeable nonvolatile (non-transitory) data storage medium in which instructions are stored that define a program or other object that may be executed by the processor 310. The data storage 318 also may include information that is recorded, on or in, the medium, and this information may be processed by the processor 310 during execution of the program. More specifically, the information may be stored in one or more data structures specifically configured to conserve storage space or increase data exchange performance. The instructions may be persistently stored as encoded signals, and the instructions may cause the processor 310 to perform any of the functions described herein. The medium may, for example, be optical disk, magnetic disk or flash memory, among others. In operation, the processor 310 or some other controller may cause data to be read from the nonvolatile recording medium into another memory, such as the memory 312, that allows for faster access to the information by the processor 310 than does the storage medium included in the data storage 318. The memory may be located in the data storage 318 or in the memory 312, however, the processor 310 may manipulate the data within the memory 312, and then copy the data to the storage medium associated with the data storage 318 after processing is completed. A variety of components may manage data movement between the storage medium and other memory elements and examples are not limited to particular data management components. Further, examples are not limited to a particular memory system or data storage system.

Although the computer system 302 is shown by way of example as one type of computer system upon which various aspects and functions may be practiced, aspects and functions are not limited to being implemented on the computer system 302 as shown in FIG. 8. Various aspects and functions may be practiced on one or more computers having a different architectures or components than that shown in FIG. 8. For instance, the computer system 302 may include specially programmed, special-purpose hardware, such as an application-specific integrated circuit (ASIC) tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 302 may be a computer system including an operating system that manages at least a portion of the hardware elements included in the computer system 302. In some examples, a processor or controller, such as the processor 310, executes an operating system. Examples of a particular operating system that may be executed include a Windows-based operating system, such as, Windows NT, Windows 2000 (Windows ME), Windows XP, Windows Vista or Windows 7 operating systems, available from the Microsoft Corporation, a MAC OS System X operating system available from Apple Computer, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular operating system.

The processor 310 and operating system together define a computer platform for which application programs in high-level programming languages may be written. These component applications may be executable, intermediate, byte-code or interpreted code which communicates over a communication network, for example, the Internet, using a communication protocol, for example, TCP/IP. Similarly, aspects may be implemented using an object-oriented programming language, such as .Net, SmallTalk, Java, C++, Ada, or C# (C-Sharp). Other object-oriented programming languages may also be used. Alternatively, functional, scripting, or logical programming languages may be used.

Additionally, various aspects and functions may be implemented in a non-programmed environment, for example, documents created in HTML, XML or other format that, when viewed in a window of a browser program, render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Thus, functional components disclosed herein may include a wide variety of elements, e.g. executable code, data structures or objects, configured to perform the functions described herein. Further, aspects and functions may be implemented in software, hardware or firmware, or any combination thereof. Thus, aspects and functions may be implemented within methods, acts, systems, system elements and components using a variety of hardware and software configurations, and examples are not limited to any particular distributed architecture, network, or communication protocol.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user mode application) or in a commonly shared data structure (such as an application registry that is defined by an operating system). In addition, some examples provide for both system and user interfaces that allow external entities to modify the parameters and thereby configure the behavior of the components.

Having thus described several aspects of at least one example, it is to be appreciated various alterations, modifications, and improvements will readily occur to those skilled in the art. Such alterations, modifications, and improvements are intended to be part of this disclosure, and are intended to be within the scope of the examples discussed herein. Accordingly, the foregoing description and drawings are by way of example only.

What is claimed is:

1. An apparatus for measuring one or more physical properties of a material flowing through a conduit, the apparatus comprising:
   a striker configured to initiate a percussion on a wall of the conduit at a position along a length of the conduit at a first location;
   a plurality of first sensors located at the position along the length of the conduit and spaced circumferentially around a perimeter of the conduit at the first location, each sensor of the plurality of first sensors being equidistant from an adjacent sensor and each sensor configured to detect an amount of energy carried by a separate spherical compression longitudinal wave generated by the striker in a direction normal to the length of the conduit;

a second sensor positioned at a second location along the length of the conduit and configured to detect the presence of spherical compression longitudinal waves generated by the striker and carried by the material in the direction of the flow of the material through the conduit, the second location disposed along the length of the conduit in a direction of the flow of the material through the conduit; and an analyzer configured to determine parameters of a decay function based on propagation of the separate spherical compression longitudinal waves detected by the plurality of first sensors and to determine a velocity of the material based on the spherical compression longitudinal waves detected by the plurality of first sensors and the spherical compression longitudinal waves detected by the second sensor.

2. The apparatus of claim 1, wherein the analyzer is further configured to determine a kinematic viscosity based on the determined parameters of the decay function.

3. The apparatus of claim 1, wherein the analyzer is further configured to determine a volumetric flow rate of the material based on the velocity of the material.

4. The apparatus of claim 3, wherein the analyzer is further configured to determine a mass flow rate of the material based on the volumetric flow rate and a density of the material.

5. The apparatus of claim 1, further comprising a level meter configured to determine the level of the material flowing through the conduit.

6. The apparatus of claim 5, wherein the analyzer is further configured to:
   determine a density of the material based in part on the level of the material; and
   determine a kinematic viscosity based in part on the density.

7. The apparatus of claim 1, wherein the conduit is at least one of partially filled with material or open.

8. The apparatus of claim 1, wherein the material is a heterogeneous liquid.

9. A method for measuring one or more physical properties of a material flowing through a conduit, the method comprising:

initiating a percussion on a wall of the conduit at a position along a length of the conduit at a first location to generate spherical compression longitudinal waves at the first location;

capturing a plurality of amplitudes of the spherical compression longitudinal wave at the position along the length of the conduit, each amplitude captured at a location spaced circumferentially around a perimeter of the conduit at the first location such that each amplitude is captured at a location that is equidistant from an adjacent captured amplitude;

capturing a response to the percussion at a second location disposed along the length of the conduit in a direction of the flow of the material through the conduit; and determining parameters of a decay function based on the captured plurality of amplitudes at the first location and determining a velocity of the material based on the captured plurality of amplitudes at the first location and the captured response at the second location.

10. The method of claim 9, further comprising determining a kinematic viscosity of the material based on the determined parameters of the decay function.

11. The method of claim 9, further comprising determining a volumetric flow rate of the material based on the velocity of the material.

12. The method of claim 11, further comprising determining a mass flow rate of the material based on the volumetric flow rate and a density of the material.

13. The method of claim 9, wherein the velocity is determined using at least one of a system of equations and a mathematical formula.

14. The method of claim 9, wherein the conduit is partially filled with the material and the method further comprises:
   determining a level of material in the conduit; and
   determining a density of the material based in part on the level of the material.

15. The method of claim 14, further comprising determining a mass flow rate based on the density and the velocity.

16. The method of claim 14, further comprising determining a kinematic viscosity based in part on the density.

* * * * *